US005645695A

United States Patent [19]

Berg

[11] Patent Number: 5,645,695
[45] Date of Patent: *Jul. 8, 1997

[54] SEPARATION OF 2-METHYL-1-PROPANOL FROM 2-METHYL-1-BUTANOL BY AZEOTROPIC DISTILLATION

[76] Inventor: Lloyd Berg, 1314 S. 3rd Ave., Bozeman, Mont. 59715

[*] Notice: The term of this patent shall not extend beyond the expiration date of Pat. No. 5,332,478.

[21] Appl. No.: 676,779

[22] Filed: Jul. 8, 1996

[51] Int. Cl.⁶ .................. B01D 3/36; C07C 29/84
[52] U.S. Cl. .................. 203/57; 203/58; 203/59; 203/60; 203/62; 203/63; 203/68; 203/69; 203/70; 568/913; 568/918
[58] Field of Search .................. 203/60, 57, 62, 203/59, 63, 58, 69, 68, 70; 568/913, 918

[56] References Cited

U.S. PATENT DOCUMENTS

| | | | |
|---|---|---|---|
| 4,204,915 | 5/1980 | Karata et al. | 203/69 |
| 5,332,478 | 7/1994 | Berg | 203/60 |
| 5,338,410 | 8/1994 | Berg | 203/60 |
| 5,338,411 | 8/1994 | Berg | 203/60 |
| 5,405,505 | 4/1995 | Berg | 203/60 |
| 5,407,542 | 4/1995 | Berg | 203/60 |
| 5,415,741 | 5/1995 | Berg | 203/60 |
| 5,417,813 | 5/1995 | Berg | 203/62 |
| 5,437,770 | 8/1995 | Berg | 203/68 |
| 5,439,561 | 8/1995 | Berg | 203/70 |
| 5,447,608 | 9/1995 | Berg | 203/69 |

*Primary Examiner*—Virgina Manoharan

[57] ABSTRACT

2-Methyl-1-propanol is difficult to separate from 2-methyl-1-butanol by conventional distillation or rectification because of the proximity of their boiling points. 2-Methyl-1-propanol can be readily separated from 2-methyl-1-butanol by azeotropic distillation. Effective agents are tetrahydrofuran, methyl acetate and toluene.

1 Claim, No Drawings

SEPARATION OF 2-METHYL-1-PROPANOL FROM 2-METHYL-1-BUTANOL BY AZEOTROPIC DISTILLATION

FIELD OF THE INVENTION

This invention relates to a method for separating 2-methyl-1-propanol from 2-methyl-1-butanol using certain organic compounds as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification..

TABLE 1

Effect of Relative Volatility on Theoretical Stage Requirements.

| Separation Purity, Both Products | Theoretical Stages at Total Reflux Relative Volatility | | | | | | | |
|---|---|---|---|---|---|---|---|---|
| (Mole Fraction) | 1.02 | 1.1 | 1.2 | 1.3 | 1.4 | 1.5 | 2.0 | 3.0 |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

2-Methyl1-propanol and 2-methyl-1-butanol boil about twenty degrees apart and have a relative volatility of 2.3 and are fairly difficult to separate by conventional rectification. Table 2 shows that to get 99% purity, fifteen actual plates are required. With an agent giving a relative volatility of 3.5, only nine actual plates are required.

TABLE 2

Theoretical and Actual Plates Required vs. Relative Volatility for 2-Methyl-1-propanol-2-Methyl-1-Butanol Separation

| Relative Volatility | Theoretical Plates Required At Total Reflux, 99% Purity | Actual Plates Required, 75% Eff. |
|---|---|---|
| 2.3 | 11 | 15 |
| 3.0 | 8 | 11 |
| 3.5 | 7 | 9 |

OBJECTIVE OF THE INVENTION

The object of this invention is to provide a process or method of azeotropic distillation that will enhance the relative volatility of 2-methyl-1-propanol to 2-methyl-1-butanol in their separation in a rectification column. It is a further object of this invention to identify effective azeotropic distillation agents that are stable and can be recycled.

SUMMARY OF THE INVENTION

The objects of this invention are provided by a process for the separation of 2-methyl-1-propanol from 2-methyl-1-butanol which entails the use of certain organic compounds when employed as the agent in azeotropic distillation.

DETAILED DESCRIPTION OF THE INVENTION

I have discovered that certain organic compounds will effectively increase the relative volatility between 2-methyl-1-propanol and 2-methyl-1-butanol during rectification when employed as the agent in azeotropic distillation. Table 3 summarizes the data obtained with these agents. The agents which are effective are butyl formate, dimethyl carbonate, methyl propionate, methyl pivalate, 3-pentanone, 3-methyl-2-butanone, 4-methyl-2-pentanone, 2-butanone, acetal, isopropyl ether, 1,4-dioxane, 2,2-dimethoxypropane, dioxolane, triethyl amine, toluene, cyclopentane, cyclohexane, cyclohexene, 1-octene, 2,2,4-trimethylpentane, diethyl amine, 2,3-dimethylpentane, methyl acetate, isobutyl acetate, propyl formate, tert.-butyl acetate,, sec.-butyl acetate, ethyl formate, methyl formate, methyl butyrate, propyl acetate, isopropyl acetate and tetrahydrofuran.

TABLE 3

Effective Azeotropic Distillation Agents For Separating 2-Methyl-1-propanol From 2-Methyl-1-butanol

| Compounds | Relative Volatility |
|---|---|
| None | 2.3 |
| Butyl formate | 2.7 |
| Dimethyl carbonate | 2.8 |
| Methyl propionate | 3.0 |
| Methyl pivalate | 3.2 |
| 3-Pentanone | 2.8 |
| 3-Methyl-2-butanone | 3.0 |
| 4-Methyl-2-pentanone | 3.2 |
| 2-Butanone | 3.7 |
| Acetal | 2.8 |
| Isopropyl ether | 2.8 |
| 1,4-Dioxane | 3.3 |
| 2,2-Dimethoxypropane | 2.9 |

TABLE 3-continued

Effective Azeotropic Distillation Agents For
Separating 2-Methyl-1-propanol From 2-Methyl-1-butanol

| Compounds | Relative Volatility |
|---|---|
| Dioxolane | 2.7 |
| Triethyl amine | 3.0 |
| Toluene | 2.9 |
| Cyclopentane | 2.7 |
| Cyclohexane | 3.2 |
| Cyclohexene | 3.0 |
| 1-Octene | 2.7 |
| 2,2,4-Trimethyl pentane | 3.0 |
| Diethyl amine | 2.8 |
| 2,3-Dimethyl pentane | 3.0 |
| Methyl acetate | 3.3 |
| Isobutyl acetate | 2.8 |
| Propyl formate | 2.7 |
| tert-Butyl acetate | 2.7 |
| sec-Butyl acetate | 2.6 |
| Ethyl formate | 3.5 |
| Methyl formate | 3.0 |
| Tetrahydrofuran | 3.4 |
| Methyl butyrate | 2.8 |
| Propyl acetate | 2.8 |
| Isopropyl acetate | 2.9 |

THE USEFULNESS OF THE INVENTION

The usefulness or utility of this invention can be demonstrated by referring to the data presented in Tables 1, 2 and 3. All of the successful agents show that 2-methyl-1-propanol can be separated from 2-methyl-1-butanol by means of azeotropic distillation and that the ease of separation is considerable.

WORKING EXAMPLE EXAMPLE 1

Fifty grams of 2-methyl-1-propanol -2-methyl-1-butanol mixture and fifty grams of tetrahydrofuran as the azeotrope forming agent were charged to a vapor-liquid equilibrium still and refluxed for two hours. The vapor composition was 84.5% 2-methyl-1-propanol and 15.5% 2-methyl-1-butanol; the liquid composition was 61% 2-methyl-1-propanol and 39% 2-methyl-1-butanol. This is a relative volatility of 3.4.

I claim:

1. A method for recovering 2-methyl-1-propanol from a mixture of 2-methyl-1-propanol and 2-methyl-1-butanol which consists essentially of distilling said mixture in the presence of an azeotrope forming agent, recovering the 2-methyl-1-propanol and the azeotrope forming agent as overhead product and obtaining the 2-methyl-1-butanol as bottoms product, wherein said azeotrope forming agent consists of one material selected from the group consisting of butyl formate, dimethyl carbonate, methyl propionate, methyl pivalate, 3-pentanone, 3-methyl-2-butanone, 4-methyl-2-pentanone, 2-butanone, acetal, isopropyl ether, 1,4-dioxane, 2,2-dimethoxypropane, dioxolane, triethyl amine, toluene, cyclopentane, cyclohexane, cyclohexene, 1-octene, 2,2,4-trimethylpentane, diethyl amine, 2,3-dimethylpentane, methyl acetate, isobutyl acetate, propyl formate, tert.-butyl acetate, sec.-butyl acetate, ethyl formate, methyl formate, methyl butyrate, propyl acetate, isopropyl acetate and tetrahydrofuran.

\* \* \* \* \*